Figure 1:
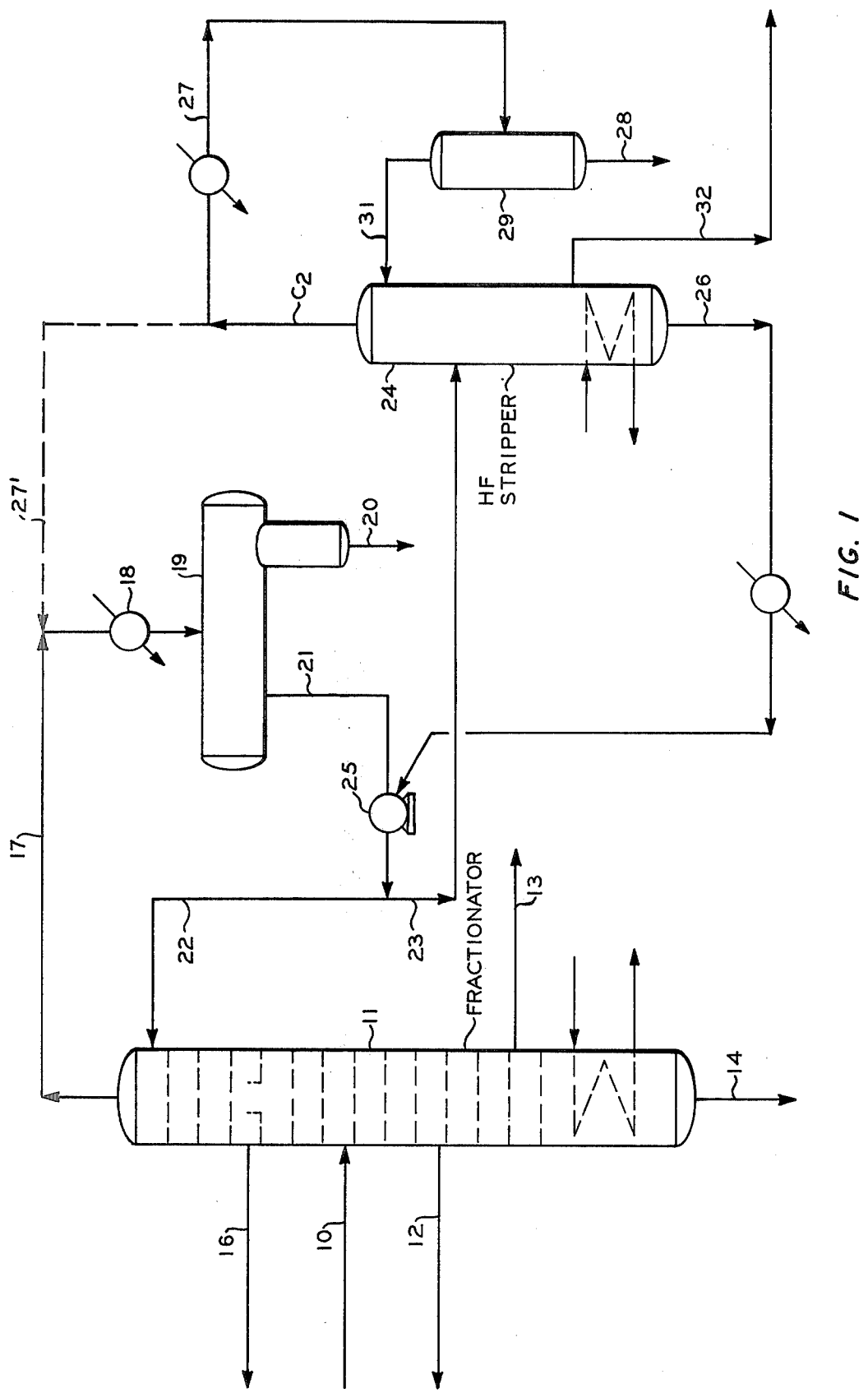

United States Patent [19]

Chapman

[11] 4,182,925
[45] Jan. 8, 1980

[54] ALKYLATION EFFLUENT RECOVERY SYSTEM

[75] Inventor: Charles C. Chapman, Bartlesville, Okla.

[73] Assignee: Phillips Petroleum Company, Bartlesville, Okla.

[21] Appl. No.: 613,667

[22] Filed: Sep. 15, 1975

Related U.S. Application Data

[63] Continuation-in-part of Ser. No. 426,674, Dec. 12, 1973, published as B 426,674 on Jan. 28, 1975 under the First Trial Voluntary Protest Program, abandoned.

[51] Int. Cl.² ............................................. C07C 3/54
[52] U.S. Cl. ................................. 585/719; 585/723
[58] Field of Search .................. 260/683.48, 683.41, 260/683.42, 683.43, 683.49, 683.51

[56] References Cited

U.S. PATENT DOCUMENTS

| B 426,674 | 1/1975 | Chapman | 260/683.41 |
|---|---|---|---|
| 2,910,521 | 10/1959 | Cobb, Jr. | 260/683.48 |
| 3,254,137 | 5/1966 | Hutto et al. | 260/683.41 |
| 3,579,603 | 5/1971 | Jones | 260/683.48 |
| 3,594,444 | 7/1971 | Jones | 260/683.48 |

Primary Examiner—George Crasanakis

[57] ABSTRACT

In the recovery of ethane and propane from an alkylation of an isoparaffin with an olefin to prevent buildup of ethane and propane in the system, the ethane and propane are taken as a side draw from the conventional HF stripper instead of being vented from the depropanizer or the fractionator overhead accumulator. Considerable ethane, propane and HF are thus saved and equipment costs reduced, especially because fractionator wall thickness can be reduced and because of the elimination of the equipment attendant the venting of the accumulator.

10 Claims, 10 Drawing Figures

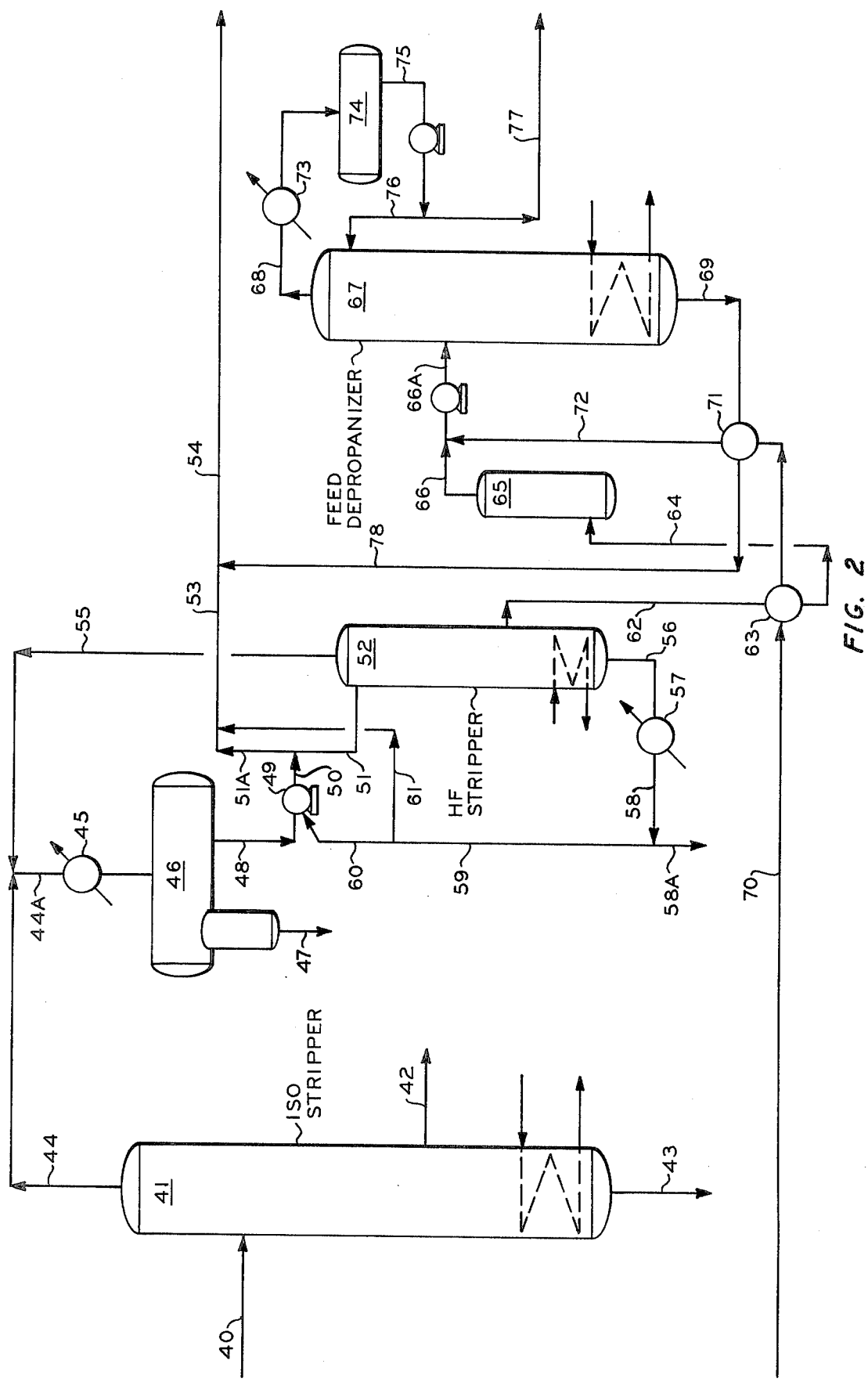

ALKYLATION EFFLUENT RECOVERY SYSTEM

This is a continuation-in-part application of my copending application having Ser. No. 426,674, filed Dec. 12, 1973, now abandoned, which was published for opposition as B 426,674 on Jan. 28, 1975.

This invention relates to the alkylation of an isoparaffin with an olefin. In accordance with a broad aspect, this invention relates to an improved recovery system following alkylation for the separation of paraffinic hydrocarbons or non-alkylatable hydrocarbons present in the olefinic feed to the alkylation that tend to buildup undesirably in the alkylation product recovery system. In one of its aspects, the invention relates to the removal of ethane from a system in which there is alkylated an isoparaffin with an olefin. In another aspect, this invention relates to the removal of propane from a system in which there is alkylated an isoparaffin with an olefin. In another of its aspects, the invention relates to a modified operation of a depropanizer or main fractionation zone in conjunction with an overhead accumulator therefor and an HF stripper for removing HF from propane and ethane to be yielded from the operation.

Conventionally, an isoparaffin, e.g., isobutane and/or isopentane, is alkylated with an olefin, e.g., at least one of propylene, a butylene, an amylene, and a hexylene, and wherein ethylene may be present, using HF acid catalyst. The hydrocarbon phase recovered from the alkylation is fractionated to recover alkylate, unreacted isoparaffin, normal paraffin (which is usually present in the isoparaffin charged to alkylation), light hydrocarbons, including propane and ethane, and HF. The fractionation means has an overhead condenser and accumulator-phase separator to which is charged the condensed fractionator overhead stream comprising ethane, propane, and HF. In one method of operation, the accumulator-phase separator is vented to remove ethane and/or propane and also HF from the system. An HF stripper is employed to separate HF from the liquid propane-rich stream recovered from the overhead accumulator-phase separator to yield an LPG propane bottoms product, which is subsequently treated to remove small quantities of HF therefrom (KOH, bauxite, and the like treatment). In another method of operation, no venting of the overhead accumulator-phase separator is used, and ethane and propane are removed together, along with some HF, as bottoms product from the HF stripper.

The improvement in the separation of the invention comprises eliminating the venting of ethane and/or propane along with the concomitant HF from the accumulator-phase separator and removing ethane along with propane or propane along with isobutane as a side draw on the HF stripper instead of as the bottoms product.

In another of its concepts, the invention provides such an operation as herein described together with the modification just described wherein the operation of the HF stripper depends upon the amount of ethane or propane present in the system. That is, when the amount of ethane in the side draw is about 1.7 liquid volume percent or less, the overhead vapor from the stripper is condensed and the condensate is returned to the overhead accumulator. When the amount of ethane in the side draw is above about 1.7 liquid volume percent, the overhead vapor from the stripper is condensed, liquid phase separation is allowed to occur, the liquid HF phase is recovered, e.g., recycled to the alkylation, and the liquid hydrocarbon phase is charged as reflux to the upper portion of the stripper.

In still another of its concepts, the invention provides for taking from the HF stripper (1) an overhead product comprising HF, (2) a side draw comprising ethane and propane, and (3) a bottoms product comprising propane, some ethane and substantially free of HF, which stream is suitable for any other use in which an HF free propane is employed, e.g., as flush for pumps in the operation. For example, the bottoms from the HF stripper, according to the invention, can be used as flush for the pump pumping the accumulator bottoms in part as reflux to the fractionator and in part as feed to the HF stripper.

In still another of its concepts, the invention provides for taking from the HF stripper (1) an overhead product comprising HF, propane and $C_4$ hydrocarbons, (2) a side draw comprising propane and isobutane which can be sent to an alkylation feed depropanizer to remove propane, and (3) a bottoms stream comprising isobutane, some propane and substantially free of HF, which stream is suitable for any other use in which an HF propane and isobutane stream is employed.

I have discovered that by taking the side draw which I have conceived be taken the attendant costs of equipment are reduced and that considerable ethane and/or propane and HF, otherwise lost, is saved. Further, there is eliminated the cost of any absorber or refrigerated tower use in conjunction with the accumulator from which normally ethane and/or propane with concomitant HF has been vented.

It is an object of this invention to provide for the alkylation of an isoparaffin with an olefin.

It is another object of this invention to provide an operation in which an isoparaffin is alkylated with an olefin in the presence of HF acid and wherein ethane in the system is to be removed.

It is another object of this invention to provide an operation in which an isoparaffin is alkylated with an olefin in the presence of HF acid and wherein propane in the system is to be removed.

It is a further object of this invention to provide for such a system as herein described in the operation of which no venting of the conventional accumulator collecting the overhead from the main fractionator or depropanizer is practiced.

It is a still further object of the invention to reduce equipment costs.

Other aspects, concepts, objects, and the several advantages of the invention are apparent from a study of this disclosure, the drawing and the appended claims.

According to the invention set forth in said copending application, in the combination operation practiced upon an alkylation effluent from which ethane is to be removed and in connection with which there are employed a fractionator, a fractionator overhead accumulator and an HF stripper, there is eliminated venting of the accumulator-phase separator and in lieu thereof a side draw of propane containing ethane is removed from the HF stripper.

According to the invention in said copending application to the extent the side draw is taken the venting of the accumulator can be eliminated. Thus, while presently preferred is an operation in which there is no venting of the accumulator and all of the ethane to be eliminated is taken as side draw from the HF stripper, it will be clear to one skilled in the art having studied this disclosure that some venting of the accumulator can be practiced while taking a side draw from the HF stripper can also be practiced.

In accordance with the present invention it has been found that the buildup of propane can be eliminated in a manner similar to the process described in said copending application by removing a side draw of isobutane and propane from an HF stripper, which side draw can be sent to the alkylation feed depropanizer where the propane can be removed and the isobutane reduced in propane content can be passed to the alkylation zone.

Thus, the invention set forth in said copending application and the present invention both apply broadly to alkylation processes where the olefinic feed charged to alkylation normally contains a paraffinic hydrocarbon or non-alkylatable material having the same number of carbon atoms or fewer carbon atoms than the olefin feed which materials tend to buildup in the recovery system and are difficult to remove without sacrifice of product quality and/or economics. Thus, the invention in said copending application generally applies to an HF alkylation wherein ethane is present in the ethylene feed to the alkylation. The present invention applies to an HF alkylation wherein propane is present in the butylenes feed to the alkylation. In said copending application ethane is concentrated in propane in the side draw from the HF stripper whereas propane is concentrated in isobutane as the side draw from the HF stripper in the present invention.

In a specific embodiment of the present invention hydrocarbon effluent from a butylenes-isobutane HF alkylation is fractionated to recover alkylate product as bottoms, an overhead comprising isobutane, propane, and HF is condensed and phase separated with HF recovery, and the lighter hydrocarbon phase is in part charged to an HF stripper from which a side draw comprising propane and isobutane is removed and charged to a feed depropanizer, preferablly after caustic treatment for HF removal. The bottoms from the HF stripper which is substantially free of HF and of propane in part is used as pump flush and the remainder is added to the bottoms yielded from the feed depropanizer, which said mixture is charged to HF alkylation as part of the feed.

In a specific embodiment of said copending application the invention comprises the steps of fractionating an alkylation effluent containing alkylate, normal butane, isobutane, propane, ethane and lighter to obtain a propane and lighter overhead vapor, condensing said stream, allowing the condensate to separate into an HF phase and a hydrocarbon phase, using at least part of the hydrocarbon phase as reflux for the fractionator and taking the remainder of the hydrocarbon phase to an HF stripper. The HF stripper is operated so as to obtain a substantially HF free propane liquid bottoms, suitable for use, for example, as pump flush, a side draw comprising propane and ethane and an overhead vapor. If the side draw contains about 1.7 or less volume percent ethane, the overhead vapor from the HF stripper is returned directly to the overhead accumulator-phase separator via the overhead condenser, and if the ethane in the side draw is about 1.7 volume percent, then the overhead vapor from the HF stripper is condensed, the condensate is allowed to separate into two phases, the HF phase is recovered, and the hydrocarbon phase is returned to the HF stripper as reflux.

A better understanding of the invention will be obtained upon reference to the drawings in which FIG. I represents diagrammatically an embodiment of the invention for the recovery of ethane present in the alkylation feed and FIG. II is another embodiment for the recovery of propane present in the olefinic feed to the alkylation Referring to FIG. I, a hydrocarbon effluent 10 from a phase separator or settler of an HF alkylation unit, not shown, wherein in the alkylation zone isobutane is alkylated with propylene-butylenes, and wherein ethane can be present in the feed, along with ethylene, is passed to fractionator 11. Isobutane vapor can be removed by 12. If can be used as a stripping fluid for an HF rerun unit, not shown. Normal butane vapor is removed at 13. Debutanized alkylate is removed at 14. Liquid isobutane which can be used to reflux the HF rerun, and as liquid recycle for HF alkylation, is recovered at 16. Vapor comprising propane, ethane, and HF is taken from tower 11 by 17 and charged through water-cooled condenser 18 to accumulator-phase separator 19 which according to the invention is not vented, thus saving considerable ethane, which will be in the LPG product, and HF. Liquid HF is removed at 20 and can be recycled to the alkylation zone. Liquid hydrocarbon comprising propane, ethane, and dissolved HF is removed from 19 and 21 and is pumped in part as reflux 22 for tower 11, and by 23 in an amount to prevent propane buildup in the system. "Stream" 23 is passed to HF stripper 24. Bottoms 26 from stripper 24, substantially free of HF and lean in ethane, and lighter, is cooled and can be used as pump flush for pump 25. Overhead vapor 27 is passed to a water-cooled condenser and the condensate is passed to accumulator-separator 29. Liquid HF is removed via 28 and can be returned to HF alkylation. Liquid hydrocarbon 31 is charged back into the top of HF stripper 24. Side draw 32 liquid comprises propane and ethane. This is the ethane which is conventionally vented from accumulator 19, or which is removed from the HF stripper as bottoms product in the liquid propane. The HF in this stream is about 0.01 pound mols per hour, or about 0.2 pound per hour on a unit which is producing about 3,400 barrels daily of alkylate 14.

When the ethane in the system is at a level such that the ethane in side draw 32 is about 1.7 volume percent or less, the overhead from the HF stripper 24 can be returned via 27' to condenser 18. This eliminates the need for condensing and reflux systems 27, 29, and 31.

When ethane is vented (no refrigeration thereon) from accumulator 19, about 1.5 pound mols per hour HF is lost with the ethane on the same size unit. When a refrigerated knock-back condenser is used on this vent gas, about 0.1 pound mols per hour of HF is lost with the ethane vented. As noted, the operation according to the invention saves both ethane and HF, by removing the ethane along with propane in the side draw from the HF stripper.

Further, the tower 11 can be operated at the conventional 300 psia and the accumulator at 110° F. The conventional operation, using no side draw from the HF stripper, would have to operate this fractionator at about 330 psia in order to remove the same amount of ethane with the propane removed as bottoms product from the HF stripper. Such higher pressure on a 10-ft. to 12-ft. diameter tower would require thicker walls at considerable extra expense.

The conventional bottoms draw-off from the HF stripper contains about 1 pound mol per hour isobutane, while the invention's side draw from the HF stripper will contain only about 0.5 pound mols per hour of isobutane.

A 2-ft. diameter HF stripper in the process of the invention will operate at about 350 psia while in the conventional operation will be at about 330 psia.

The following data obtained by computer design calculation further illustrate the invention and its attendant advantages.

| Typical Operation | | |
|---|---|---|
| Operating Conditions: | | |
| Tower 11: | | |
| Top Temperature, °F. | 128 | ( 53.3° C.) |
| Bottom Temperature, °F. | 439 | ( 226° C.) |
| Pressure, psia | 300 | (2050 KPa) |
| Accumulator 19: | | |
| Temperature, °F. | 110 | ( 43.3° C.) |
| Pressure, psia | 295 | (2000 KPa) |
| HF Stripper 24: | | |
| Top Temperature, °F. | 120 | ( 48.9° C.) |
| Bottom Temperature, °F. | 153 | ( 69.2° C.) |
| Pressure, psia | 350 | (2400 KPa) |
| Accumulator 29: | | |
| Temperature, °F. | 100 | ( 37.8° C.) |
| Pressure, psia | 345 | (2350 KPa) |
| Elevation above Reflux, ft. | 5 | ( 1.53 m) |

TABLE I

| STREAM | 10 | 12 | 13 | 14 | 16 | 17 | 21 | 22&23** | 26 | 27 | 31 | 32 |
|---|---|---|---|---|---|---|---|---|---|---|---|---|
| | | | | | POUND MOLS/HOUR | | | | | | | |
| Ethane and Lighter | 6.8 | .4 | — | — | 1.2 | 83.7 | 83.4 | 83.48 | .08 | 7.0 | 7.0 | 4.9 |
| Propane | 360.0 | 97.9 | — | — | 149.0 | 2224.0 | 2221.5 | 2245.0 | 23.5 | 34.4 | 34.4 | 110.5 |
| Isobutane | 2900.0 | 1395.0 | 2.6 | .6 | 1501.0 | 22.8 | 22.8 | 23.4 | .6 | .08 | .08 | .8 |
| Normal Butane | 607.0 | 282 | 43.8 | 27.0 | 254.2 | — | — | — | — | — | — | — |
| Pentanes Plus | 381.0 | 21 | 3.6 | 343.0 | 13.4 | — | — | — | — | — | — | — |
| HF | 140 | 5 | — | — | 20.0 | 193 | 83 | 83 | (0.000015) | 6.0 | 1.0 | (.005) |
| | 4394.8 | 1801.3 | 50.0 | 370.6* | 1938.8 | 2523.5 | 2410.7 | 2434.88 | 24.18 | 47.48 | 42.48 | 116.2 |
| | | | | | MOL PERCENT | | | | | | | |
| Ethane and Lighter | .15 | .02 | — | — | .06 | 3.32 | 3.46 | 3.43 | .33 | 14.74 | 16.48 | 4.22 |
| Propane | 8.19 | 5.43 | — | — | 7.69 | 88.13 | 92.15 | 92.20 | 97.19 | 72.45 | 80.98 | 95.09 |
| Isobutane | 65.99 | 77.44 | 5.2 | .16 | 77.42 | .90 | .95 | .96 | 2.48 | .17 | .19 | .69 |
| Normal Butane | 13.81 | 15.65 | 87.6 | 7.29 | 13.11 | — | — | — | — | — | — | — |
| Pentanes Plus | 8.67 | 1.18 | 7.2 | 92.55 | .69 | — | — | — | — | — | — | — |
| HF | 3.19 | .28 | — | — | 1.03 | 7.65 | 3.44 | 3.41 | trace | 12.64 | 2.35 | trace |
| | 100.0 | 100.0 | 100.0 | 100.0* | 100.00 | 100.00 | 100.00 | 100.00 | 100.00 | 100.00 | 100.00 | 100.00 |

*3400 Barrels/Day Debutanized Alkylate-(Pentane Plus).
**Includes pump flush 26.
Feed to 24 is sum of 26, 28 and 32.
(HF is hydrofluoric acid)

While in the drawing there have been shown several streams taken from fractionator 11, it will be understood that normal butane can be taken along with the bottoms and later separated therefrom. Further, other modifications known in the art can be practiced. Essentially the overhead 17 is of primary concern in this description. It will be noted that the venting of accumulator 19 either periodically or continuously has been eliminated according to a preferred embodiment.

The following approximate ranges of pressures and temperatures can be observed in the operation of the overhead accumulator and in the HF stripper:

| Accumulator: | | |
|---|---|---|
| Pressure, psia | 200 to 450 | (1370 to 3100 KPa) |
| Temperature, °F. | 70 to 150 | (21.1° to 65.6° C.) |
| HF Stripper: | | |
| Pressure, psia | 250 to 450 | (1725 to 3100 KPa) |
| Temperature, °F. | 100 to 150 | (37.8° to 65.6° C.) |

The pressures and temperatures selected will depend, in part, upon the compositions of the streams, the condensing temperature available, etc.

It is pointed out that as the ethane content of the fractionator overhead increases, the pressure on the system must be increased in order to condense this overhead at the same (cooling water) condensing temperature.

Referring now to FIG. II, a hydrocarbon effluent 40 from a phase separator or settler of an HF alkylation unit, not shown, in which isobutane is alkylated with butylene, and wherein propane can be present in the butylenes feed is passed to isostripper or fractionator 41. Fractionator 41 is operated under conditions such that normal butane vapor is removed as a side draw by line 42 and debutanized alkylate product is removed as bottoms by way of line 43. An overhead stream comprising propane, isobutane, normal butane, and some HF and some isopentane and heavier hydrocarbons is passed by way of line 44, line 44a to condenser 45 and passed to accumulator-phase separator 46 which, according to the invention, is not vented. Liquid HF is removed at 47 and can be recycled to the alkylation zone.

A liquid hydrocarbon stream comprising propane, isobutane, normal butane, some heavier hydrocarbon and some HF is removed from accumulator-phase separator 46 by way of line 48, passed through pump 49, line 50, and part of a stream is passed as feed by way of line 51 to HF stripper 52. The remainder of stream 50 is passed by way of line 53 and 54 as part of the feed to the alkylation zone not shown.

The liquid hydrocarbon stream introduced into HF stripper 52 by way of line 51 is subjected to conditions such that HF is taken overhead by way of line 55 along with some propane, isobutane, and normal butane which is returned via line 44a to condenser 45 and combined with the overhead from isostripper 41. The bottoms stream comprising isobutane and very little propane and other hydrocarbons is removed from stripper 52 by way of line 56, passed through cooler 57, and thence through lines 58 and 59, and can be used as pump flush, for pump 49, by passage through line 60. A major portion of stream 59 is passed through line 61 and combined with the liquid hydrocarbon stream 48, removed from accumulator 46, and is passed through line 53 and line 54 to the alkylation zone as part of the feed. Additional pump flush (substantially HF-free) is recovered via line 58a. In accordance with the invention a side draw stream 62 comprising propane and isobutane is removed from HF stripper, passed through heat exchanger 63, and thence by line 64 passed through caustic treater 65 and introduced by line 66 and line 66a into feed depropanizer 67 wherein the stream is subjected to fractionation conditions such that propane is taken overhead by line 68 and isobutane is bottoms by line 69. Alkylation feed comprising olefins and isoparaffins is introduced by line 70, passed through heat exchanger 63 and 71, and combined with line 66 by way of line 72 as the remainder of the feed to depropanizer 67. The feed in this embodiment comprises propylene, propane, isobutane, butylene, normal butane and some higher boiling hydrocarbon.

Depropanizer 67 is operated under conditions such that propylene, propane and some C4 hydrocarbon are taken overhead by line 68, passed through condenser 73, thence introduced into accumulator 74. The condensed hydrocarbons are removed by line 75 and part is returned by line 76 as reflux to column 67 and the remainder removed for further use as desired by way of line 77.

The bottoms stream 69 removed from depropanizer 67 comprises isobutane, butylenes, normal butane, and some propylene and propane and is passed through heat exchanger 71, thence by line 78 in combination with the hydrocarbon mixture in line 53 and passed by way of line 54 as feed to the alkylation zone not shown.

The following calculated data further illustrate the embodiment of the invention described in FIG. II and its attendant advantages.

| Typical Operation | | |
|---|---|---|
| Operating Conditions: | | |
| Tower 41: | | |
| Top Temperature, °F. | 162 | ( 72.2° C.) |
| Bottom Temperature, °F. | 325 | ( 162.8° C.) |
| Pressure, psia | 150 | (1030 KPa) |
| Accumulator 46: | | |
| Temperature, °F. | 110 | ( 43.3° C.) |
| Pressure, psia | 135 | ( 920 KPa) |
| HF Stripper 52: | | |
| Top Temperature, °F. | 138 | ( 58.9° C.) |
| Bottom Temperature, °F. | 180 | ( 82.2° C.) |
| Pressure, psia | 200 | (1370 KPa) |
| Depropanizer 67: | | |
| Top Temperature, °F. | 112 | ( 44.4° C.) |
| Bottom Temperature, °F. | 212 | ( 100° C.) |
| pressure, psia | 250 | (1725 KPa) |
| Accumulator 74: | | |
| Temperature, °F. | 105 | ( 40.6° C.) |
| Pressure, psia | 240 | (1650 KPa) |

TABEL II

| STREAM | 44 | 55 | 44A | 47 | 48 | 60 | 50 | 51A | 51 | 58 | 58A | 61 |
|---|---|---|---|---|---|---|---|---|---|---|---|---|
| BARRELS/DAY | | | | | | | | | | | | |
| HF | 90 | 3 | 93 | 37 | 56 | | 56 | 53 | 3 | | | |
| $C_3$ | 1,054 | 8 | 1,062 | | 1,062 | 4 1,066 | 1,011 | 55 | 13 | 4 | 5 | |
| $IC_4$ | 10,810 | 33 | 10,843 | 3 | 10,840 | 123 | 10,963 | 10,397 | 566 | 389 | 123 | 143 |
| $nC_4$ | 1,165 | 3 | 1,168 | | 1,168 | 15 | 1,183 | 1,122 | 61 | 46 | 15 | 16 |
| $C_5+$ | 144 | | 144 | | 144 | 2 | 146 | 138 | 8 | 8 | 2 | 4 |
| | 13,263 | 47 | 13,310 | 40 | 13,270 | 144 | 13,414 | 12.721 | 693 | 456 | 144 | 168 |

| STREAM | 53 | 62 | 72 | 66A | 77 | 69 | 54 |
|---|---|---|---|---|---|---|---|
| HF | 53 | | | | | | 53 |
| $C_3=$ | | | 499 | 499 | 491 | 8 | 8 |
| $C_3$ | 1,016 | 34 | 550 | 584 | 562 | 22 | 1,038 |
| $IC_4$ | 10,540 | 144 | 458 | 602 | 8 | 594 | 11,134 |
| $C_4='s$ | | | 850 | 850 | 4 | 846 | 846 |
| $NC_4$ | 1,138 | 12 | 338 | 350 | | 350 | 1,488 |
| $C_5+$ | 142 | | 20 | 20 | | 20 | 20 |
| | 12,889 | 190 | 2,715 | 2,905 | 1,065 | 1,840 | 14,587 |

$C_3=$, $C_4='s$ mean propylene and butylenes, respectively.

Operation in accordance with the foregoing embodiment wherein a vapor side draw of isobutane and propane is withdrawn from the HF stripper, the stream sent to the feed depropanizer 67 has a higher concentration of propane and therefore the stream is reduced in volume. In this case the propane in the recycle is reduced by about 23 percent and the overall heat required is reduced by about 4 percent. Thus, using a side draw and the HF stripper to remove propane and isobutane will: (1) remove a given amount of propane and reduce propane in the recycle at a reduced utilities cost, and (2) remove the higher volume of propane with no increase in utilities or propane in the recycle.

The following approximate ranges of pressures and temperatures can be observed in the operation of the overhead accumulator and the HF stripper and feed depropanizer in accordance with the embodiment described in FIG. II:

| Accumulator 46: | | |
|---|---|---|
| Pressure, psia | 125 to 220 | (860 to 1500 KPa) |
| Temperature, °F. | 100 to 150 | (37.8° to 65.6° C.) |
| HF Stripper 52: | | |
| Pressure, psia | 125 to 300 | (860 to 2050 KPa) |
| Top Temperature, °F. | 100 to 140 | (37.8° to 60° C.) |
| Bottom Temperature, °F. | 135 to 215 | (57.2° to 101.7° C.) |
| Feed Depropanizer 67: | | |
| Pressure, psia | 200 to 300 | (1370 to 2050 KPa) |
| Top Temperature, °F. | 100 to 125 | (37.8° to 51.7° C.) |
| Bottom Temperature, °F. | 175 to 250 | (79.4 to 121.1° C.) |

The pressures and temperatures selected will depend in part upon the compositions of the streams, condensing temperature available, etc.

Reasonable variation and modification are possible within the scope of the foregoing disclosure, the drawing and the appended claims to the invention the essence of which is that in an alkylation of isoparaffin with olefin in which the alkylation effluent stream is treated to recover alkylate, various streams and to remove ethane and/or propane from the system and wherein the ethane and/or propane is removed with use of a depropanizer, and attendant overhead accumulator and HF stripper, as described, the venting of the accumulator has been eliminated substantially and there is in lieu of such venting a side draw of propane containing ethane or isobutane containing propane from the HF stripper, thus saving equipment costs and ethane and/or propane and HF normally lost heretofore as well as a stream substantialy free from HF acid which can be used as a pump flush or for other purposes as may be desired.

I claim:

1. In the alkylation of an isoparaffin with an olefin wherein the alkylation effluent hydrocarbon phase is fractionated to remove alkylate, normal butane, isobutane, ethane and lighter, and HF acid therefrom, wherein the overhead hydrocarbon fraction containing propane, ethane, lighter hydrocarbons and HF acid is condensed and allowed to separate into phases in the fractionator overhead accumulator and said HF acid is removed while the condensed hydrocarbon phase is in part returned as reflux to said fractionator and in part is passed to an HF stripper, the improvement which comprises removing ethane and propane as a side draw stream from said HF stripper, thus obtaining a bottoms of liquid propane from the HF stripper, substantially free from HF, suitable for use wherever a hydrocarbon stream free from HF is needed.

2. An operation according to claim 1 wherein in said HF stripper, whenever the ethane is about 1.7 volume percent or less in the side draw, the overhead vapor from the stripper is condensed and returned directly to said accumulator.

3. An operation according to claim 1 wherein the ethane is above about 1.7 volume percent in the side draw, the overhead vapor from the stripper is condensed, HF acid is separated therefrom, and the liquid hydrocarbon phase is returned to said HF stripper as reflux.

4. In the alkylation of an isoparaffin with an olefin wherein the alkylation effluent hydrocarbon phase is fractionated to remove alkylate, normal butane, isobutane, propane, and HF acid therefrom, wherein the overhead hydrocarbon fraction containing propane, isobutane and some normal butane and HF acid is condensed and allowed to separate into phases in the fractionator overhead accumulator and said HF acid is removed while the condensed hydrocarbon phase is in part passed to an HF stripper, the improvement which comprises removing propane and isobutane as a side draw stream from said HF stripper, thus obtaining a bottoms of liquid isobutane from the HF stripper, substantially free from HF, suitable for use wherever a hydrocarbon stream free from HF is needed.

5. A process according to claim 4 wherein said side draw is passed along with alkylation feed comprising olefins and isoparaffin to a feed depropanizing zone wherein propane and lighter hydrocarbon are removed overhead and bottoms stream recovered substantially freed of propane is passed to an alkylation zone as a hydrocarbon feed.

6. A process according to claim 5 further comprising the step of passing at least a part of the bottoms removed from HF stripper as part of the feed to the alkylation.

7. A process according to claim 6 further comprising the step of passing the remainder of the condensed hydrocarbon phase recovered from said accumulator as part of the feed to the alkylation.

8. A process for the recovery of propane and ethane introduced and produced during alkylation which comprises the steps of:
(a) reacting isobutane and an olefin also containing ethane in the presence of HF under conditions which produce alkylate,
(b) passing the reaction effluent hydrocarbon phase to a distillation zone and therein subjecting said effluent phase to distillation conditions such that the effluent is separated into a bottoms alkylate stream, a normal butane side stream, an isobutane side stream, and an overhead comprising HF, propane, and ethane,
(c) condensing said overhead and recovering a liquid hydrocarbon phase and passing at least part of said condensed liquid hydrocarbon phase to an HF stripper, and
(d) subjecting said liquid hydrocarbon phase to stripping conditions in said HF stripper to recover overhead an HF-containing stream, a bottoms propane stream substantially free of HF, and a side draw stream comprising ethane and propane.

9. An improved process for the recovery of paraffinic impurity introduced and/or produced during alkylation which comprises the steps of:
(a) reacting isobutane and an olefin alkylating agent also containing propane in the presence of HF under conditions which produce alkylate,
(b) passing the reaction effluent hydrocarbon phase to a distillation zone and therein subjecting said effluent phase to distillation conditions such that the effluent is separated into a bottoms alkylate stream, a normal butane side stream, and an overhead containing HF acid, propane, isobutane, and some normal butane,
(c) condensing said overhead and recovering a liquid hydrocarbon phase and passing at least part of said condensed liquid hydrocarbon phase to an HF stripper,
(d) subjecting said liquid hydrocarbon phase to stripping conditions in said HF stripper to recover overhead an HF-containing stream, a bottoms isobutane stream substantially free of HF, and a side draw stream containing propane and isobutane, and
(e) passing said side draw along with alkylation feed comprising olefins, propane, and isoparaffin to a feed depropanizing zone operated under distillation conditions such that propane and lighter hydrocarbons are removed overhead and isobutane substantially free of propane is removed as a bottoms stream and is passed to an alkylation zone as at least part of the hydrocarbon feed.

10. A process according to claim 9 further comprising the steps of:
(f) passing at least a part of said bottoms removed from said HF stripper as part of the feed to said alkylation and
(g) passing the remainder of the condensed hydrocarbon phase recovered in (c) as part of the feed to said alkylation.

* * * * *